(12) United States Patent
Ellson et al.

(10) Patent No.: US 7,854,343 B2
(45) Date of Patent: Dec. 21, 2010

(54) FLUID CONTAINERS WITH RESERVOIRS IN THEIR CLOSURES AND METHODS OF USE

(75) Inventors: Richard N. Ellson, Palo Alto, CA (US); Michael F. Miller, Mountain View, CA (US); Arlen Mark Bramwell, Sebastopol, CA (US)

(73) Assignee: Labcyte Inc., Sunnyvale, CA (US)

( * ) Notice: Subject to any disclaimer, the term of this patent is extended or adjusted under 35 U.S.C. 154(b) by 1175 days.

(21) Appl. No.: 11/077,630

(22) Filed: Mar. 10, 2005

(65) Prior Publication Data

US 2006/0201948 A1 Sep. 14, 2006

(51) Int. Cl.
*B65D 51/18* (2006.01)
(52) U.S. Cl. ............... 220/256.1; 220/507; 422/40; 422/100
(58) Field of Classification Search ........... 220/507, 220/256.1; 422/40, 61, 100; 435/307.1; 436/180
See application file for complete search history.

(56) References Cited

U.S. PATENT DOCUMENTS

| | | | | | |
|---|---|---|---|---|---|
| 2,186,908 | A | * | 1/1940 | Page et al. ................. | 215/248 |
| 3,693,804 | A | * | 9/1972 | Grover ...................... | 210/359 |
| 3,832,141 | A | * | 8/1974 | Haldopoulos ............... | 422/101 |
| 3,846,077 | A | * | 11/1974 | Ohringer .................... | 422/100 |
| 4,296,205 | A | * | 10/1981 | Verma ....................... | 435/401 |
| 4,501,360 | A | * | 2/1985 | Levy et al. .................. | 206/443 |
| 4,671,405 | A | * | 6/1987 | Hagan ....................... | 206/139 |
| 4,774,962 | A | * | 10/1988 | Hebel et al. ................ | 600/573 |
| 4,885,253 | A | * | 12/1989 | Kralovic .................... | 435/287.4 |
| 5,103,836 | A | * | 4/1992 | Goldstein et al. ........... | 600/573 |
| 5,511,558 | A | * | 4/1996 | Shepard et al. ............. | 600/573 |
| 5,527,513 | A | * | 6/1996 | Burns ........................ | 422/102 |
| 5,552,325 | A | * | 9/1996 | Nochumson et al. ........ | 436/177 |
| 5,612,218 | A | * | 3/1997 | Busch et al. ............... | 435/288.1 |

(Continued)

FOREIGN PATENT DOCUMENTS

EP 1 364 710 A 11/2003

(Continued)

OTHER PUBLICATIONS

International Search Report for application PCT/US2006/008572.

(Continued)

*Primary Examiner*—Anthony Stashick
*Assistant Examiner*—Christopher B McKinley
(74) *Attorney, Agent, or Firm*—Jones Day

(57) ABSTRACT

Fluid containers are disclosed which have fluid reservoirs in their closures. These reservoirs are advantageous to hold sacrificial fluid which lessens the loss of the fluid of interest to the outside through evaporation. The reservoirs may have openings to the inside or outside of the container, or to both. Reservoirs with openings to the outside serve to reduce evaporative loss by raising the partial pressure of fluid in the vicinity of the contact between the closure and the remainder of the container. The reservoirs may be refillable without opening the container. In one embodiment a fluid reservoir allows the zone of contact between the closure and the remainder of the container to be immersed in fluid, so that gases seeking to escape the interior of the container must pass through fluid.

15 Claims, 5 Drawing Sheets

U.S. PATENT DOCUMENTS

| | | | |
|---|---|---|---|
| 5,786,227 A * | 7/1998 | Charlton | 436/177 |
| 5,856,172 A * | 1/1999 | Greenwood et al. | 435/260 |
| 5,955,032 A * | 9/1999 | Kelly et al. | 422/100 |
| 5,981,293 A * | 11/1999 | Charlton | 436/177 |
| 6,027,694 A * | 2/2000 | Boulton et al. | 422/102 |
| 6,106,783 A * | 8/2000 | Gamble | 422/102 |
| 6,136,273 A * | 10/2000 | Seguin et al. | 422/99 |
| 6,145,688 A * | 11/2000 | Smith | 220/259.3 |
| 6,193,088 B1 * | 2/2001 | Vincent et al. | 215/261 |
| 6,202,878 B1 * | 3/2001 | Cook | 220/255 |
| 6,375,028 B1 * | 4/2002 | Smith | 220/258.1 |
| 6,500,390 B1 * | 12/2002 | Boulton et al. | 506/43 |
| 6,565,813 B1 | 5/2003 | Garyantes | |
| 6,716,392 B1 * | 4/2004 | Putcha et al. | 422/61 |
| 6,939,513 B2 * | 9/2005 | Berray et al. | 422/99 |
| 7,176,034 B2 * | 2/2007 | Efthimiadis et al. | 436/177 |
| 7,435,389 B2 * | 10/2008 | Anderson et al. | 422/100 |
| 7,537,935 B2 * | 5/2009 | Bienhaus et al. | 436/177 |
| 2002/0090737 A1 * | 7/2002 | Levin et al. | 436/180 |
| 2002/0130100 A1 * | 9/2002 | Smith | 215/247 |
| 2003/0108450 A1 * | 6/2003 | Mainquist et al. | 422/99 |
| 2003/0124549 A1 | 7/2003 | Beutler et al. | |
| 2003/0150257 A1 * | 8/2003 | Mutz et al. | 73/61.49 |
| 2005/0048575 A1 * | 3/2005 | Coassin et al. | 435/7.1 |

FOREIGN PATENT DOCUMENTS

| | | |
|---|---|---|
| WO | WO 01/07161 | 2/2001 |
| WO | WO 2005/000469 A | 1/2005 |

OTHER PUBLICATIONS

Fillers, Automated Microplate Sealing and Unsealing with SealTite, TekCel Poster, http://lab-robotics.org/Presentation/Posters/Poster2038.pdf.

* cited by examiner

FLUID CONTAINERS WITH RESERVOIRS IN THEIR CLOSURES AND METHODS OF USE

TECHNICAL FIELD

This invention relates generally to containers for fluids, and in particular to containers for small quantities of fluid used in chemical and biomedical research and development.

BACKGROUND

In chemical and biomedical research and development, it is common to manipulate large numbers (e.g., thousands) of fluid containers which must be readily and automatably opened and closed, and yet must also be stored for months or years. The need to open and close the containers readily tends to induce the use of relatively poorly sealed containers, whereas the desire to store the containers for months or years tends to make it desirable to achieve tight sealing, for example to avoid evaporation loss and contamination from the outside.

The fluid containers used in chemical and biomedical research are subject to substantial chemical compatibility constraints, for example that they should not be made of materials which would be attacked by the solvents which they are designed to hold. Such constraints will also apply to the closures of such fluid containers. Adhesives are generally not preferred for closure of such fluid containers because of concerns about contamination and nonuniformity arising from adhesive residue left over from one closure to the next.

Examples of fluid containers widely used in chemical and biomedical research and development are well plates and micro tubes. Well plates are commonly used which have 96, 384, and 1536 wells, although other numbers of wells are also in use. The dimensions and other characteristics of well plates have been standardized by the Society for Biomolecular Screening. A common size of well plate is 127.76 by 85.48 by 14.35 mm. Well plates are commonly designed to be stacked on top of each other in storage. Microtubes are commonly used in racks of 96 or 384. These racks of microtubes conform to dimensions similar to the length and width of well plates so they can be handled by similar robotic and automation equipment.

For well plates, a wide variety of lids have been developed. An example of a well plate lid of the prior art is described in U.S. Patent Application Publication No. 2003/0108450. That well plate lid uses the weight of the lid to provide the force which holds the lid to the well plate. The lid is stated to weigh 400 g preferably. A compliant sealing member, preferably of silicone rubber, forms part of the lid and is pressed against the well plate.

A commercially available lid for well plates is the SealTite lid from TekCel, Inc. (Hopkinton, Mass.). The SealTite lid has a metal spring/clamp structure to form a better seal than would be possible if the weight of the lid were the only force holding the lid to the well plate. The use of force as provided, for example, by a spring/clamp may give rise to difficulties in automation of the handling of well plates with lids. See in this regard the TekCel poster at http://lab-robotics.org/Presentations/Posters/Poster2038.pdf.

There have also been efforts in the art to adapt to evaporation losses. In particular, in some cases the outer wells of a well plate are not used to hold fluids of interest but instead are filled with a volume of the solvent in which those fluids are stored. This solvent in the outer wells has been observed to reduce the rate at which the solvent in the inner wells evaporates. The outer wells are sometimes referred to as "moat wells" when so used.

An alternative means to adapt to evaporation losses is to periodically audit the fluid levels in the reservoirs of the container and to add solvent to those reservoirs as needed. United States Patent Application Publication No. 2003/0150257 describes a convenient automatable way of carrying out the auditing by means of focused acoustic energy.

There is therefore a need in the art to adapt to the evaporation losses caused by less than perfect seals which are used in order to facilitate the automated opening and closing of containers which hold small quantities of fluid.

SUMMARY OF THE INVENTION

In a preferred embodiment of the invention, a container has a closure. The container has a primary member which contains one or more reservoirs for fluids of interest. The primary member could be, for example, a well plate or a test tube or minitube. The closure also contains one or more fluid reservoirs. At least some of these reservoirs have openings which open into the interior of the container when it is closed using the closure. Preferably, these openings are near the zone at which the closure contacts the primary member, referred to as the "contact zone."

In an alternative preferred embodiment of the invention, a container has a closure. The container has a primary member which contains one or more reservoirs for fluids of interest. The primary member could be, for example, a well plate, a test tube or a collection of minitubes in a rack. The closure also contains one or more fluid reservoirs. At least some of these reservoirs have openings which open into the exterior of the container when it is closed using the closure, in the vicinity of the contact zone where the closure meets the primary member.

In a further preferred embodiment of the invention, a closure reservoir is designed so that the portion of the primary member which contacts the closure is partially surrounded by fluid when the closure and the primary members are in contact. Thus, this reservoir opens both into the interior and the exterior of the container when the latter is closed.

In a further preferred embodiment of the invention, there are provided methods of storing fluids in containers. In certain methods of the invention, a fluid sample comprising a solvent is stored in a reservoir. The reservoir is covered using a closure which has one or more closure reservoirs. The closure reservoirs contain quantities of the solvent. The solvent in the closure reservoirs is replenished.

DRAWINGS

DETAILED DESCRIPTION OF EMBODIMENTS OF THE INVENTION

Figure 1A:
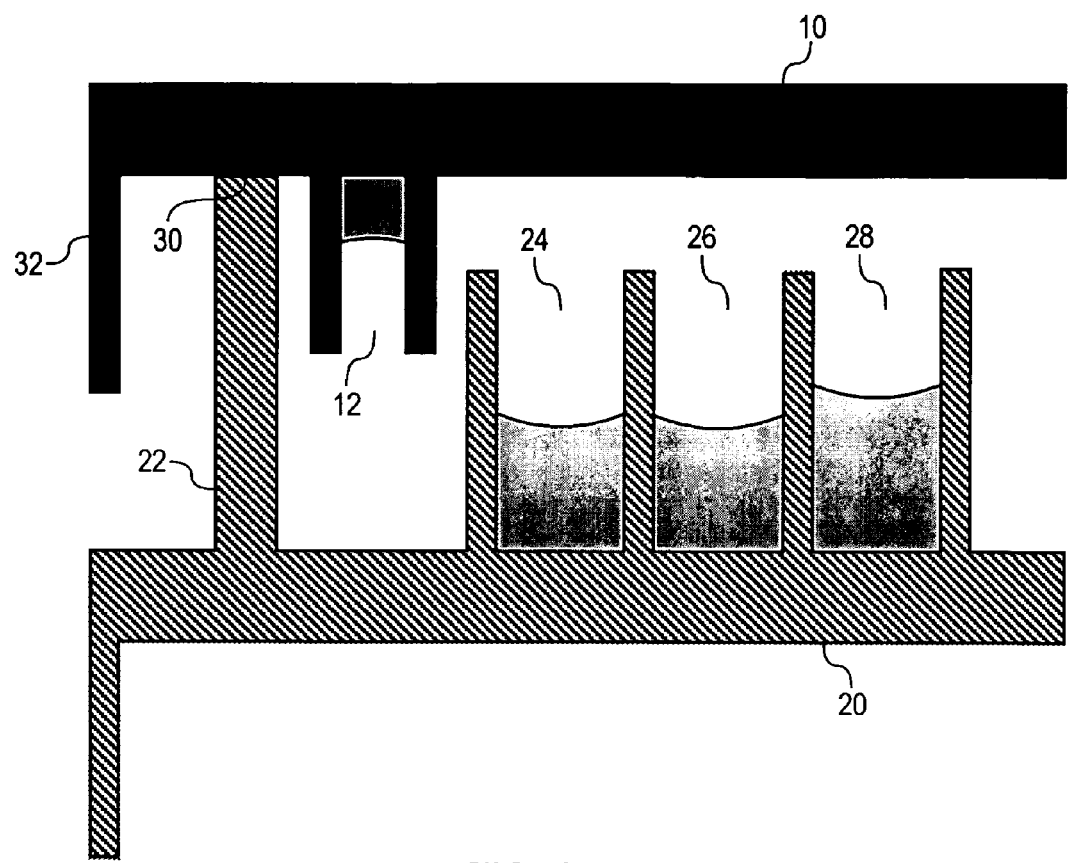
FIGS. 1A-1B depict a schematic cross section and bottom view of a closure with a reservoir, the closure being designed for a well plate.

Before describing the present invention in detail, it is to be understood that this invention is not limited to specific fluids, biomolecules, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include both singular and plural referents unless the context clearly dictates otherwise. Thus, for example, reference to "a reservoir" includes a plurality of reservoirs as well as a single reservoir, reference to "a droplet" includes a plurality of droplets as well as single droplet, and the like.

In describing and claiming the present invention, the following terminology will be used in accordance with the definitions set out below.

The term "fluid" as used herein refers to matter that is nonsolid, or at least partially gaseous and/or liquid, but not entirely gaseous. A fluid may contain a solid that is minimally, partially, or fully solvated, dispersed, or suspended. Examples of fluids include, without limitation, aqueous liquids (including water per se and salt water) and nonaqueous liquids such as organic solvents and the like. As used herein, the term "fluid" is not synonymous with the term "ink" in that an ink must contain a colorant and may not be gaseous.

"Optional" or "optionally" means that the subsequently described circumstance may or may not occur, so that the description includes instances where the circumstance occurs and instances where it does not.

The term "reservoir" as used herein refers to a receptacle or chamber for containing a fluid. A reservoir may also be a volume of a member within which a fluid is constrained or held.

The term "closure" as used herein refers to a member used to close a container for fluids. It thus encompasses for example lids, stoppers, and caps. A container may be closed with one closure or, in some cases, with multiple closures. Closures normally meet with containers at respective surfaces on each member. The mechanical match of the closure and container at the surfaces where they meet may not be perfect, so that some exchange of vapor between the inside and outside of the container may be possible even with closures in place.

In a preferred embodiment of the invention, a container has a closure. The container has a primary member which contains one or more reservoirs for fluids of interest. The primary member could be, for example, a well plate or a test tube. The closure also contains one or more fluid reservoirs. At least some of these reservoirs have openings which open into the interior of the container when it is closed using the closure. Preferably, these openings are near the zone at which the closure contacts the primary member, referred to as the "contact zone."

In a use of the container of the preceding embodiment, the fluids of interest are held within the reservoirs of the container. A solvent which the fluids of interest comprise is held in one or more closure reservoirs. The solvent evaporates from both the fluids of interest and from the closure reservoirs. If the seal between container and closure were perfect the evaporation would reach an equilibrium when the partial pressure of the solvent in the interior of the container equaled the vapor pressure of the solvent. However, the inevitable imperfections of the seal mean that there will be slow diffusion of the vapor-phase solvent into the external atmosphere. The rate of this diffusion may be expected to relate to the difference in partial pressure of the solvent immediately inside and immediately outside the seal. Just as with the "moat wells" referred to above, the reservoirs of solvent in the closure may be expected to reduce the rate at which solvent evaporates from the fluids of interest. The solvent in the closure reservoirs may be viewed as "sacrificial" solvent which is used for the purpose of sparing the solvent employed in the fluids of interest so as to prevent the premature evaporation of the solvent in the fluids.

The fluids of interest in the invention may be any fluid which is being used in research, development, or in some cases manufacturing and education. In particular, the fluids of interest may contain biological samples such as living organisms or materials derived from such organisms. They may form part of libraries of compounds generated through combinatorial chemistry or otherwise. They may comprise biomolecules or they may comprise synthetic or naturally occurring organic or inorganic molecules.

The reservoirs in the closure may be of a wide variety of shapes. They may be simple indentations, for example of hemispherical or cylindrical shape, arranged around the contact zone on the inside of the closure. A reservoir may simply be a groove arranged around the contact zone on the inside of the closure. Alternatively, it may be a compartment of substantial size spanning much of the closure.

Figure 1B:
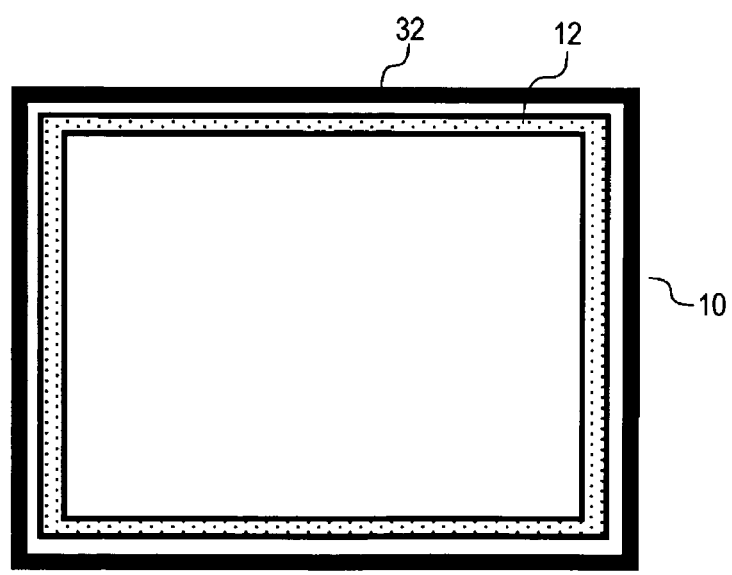

FIGS. 1A and 1B show a schematic partial cross section and bottom view of a closure 10 of the invention. FIG. 1A also depicts a portion of a primary member 20 in contact with closure 10 at a contact zone 30. Contact is achieved with a projection 22 of the primary member. The primary member 20 has a number of reservoirs 24, 26, 28 which can hold fluids of interest. In FIG. 1A, we see that the closure 10 has a reservoir 12 for a quantity of fluid. In the bottom view in FIG. 1B, we see that this reservoir is a continuous channel that goes around the entire outer edge of the closure 10. The outer edge of the closure 10 also has a lip 32 which also goes around the entire edge. Although this is not shown, primary member 20's projection 22 would also go around the entire edge of the primary member.

It has been observed that when small drops of fluid attach, to suitable surfaces, they remain in place when the surfaces are moved into different orientations with respect to the earth's gravitational force. For example, a droplet may remain attached to a surface when it is upside down. The reason for this is that for small droplets the pull of gravity is small compared to surface forces. If one considers a series of droplets of the same shape and different sizes, the weight—and thus gravitational pull—are proportional to the third power of the droplet size whereas surface forces are only proportional to the second power of droplet size. Because of this, at smaller droplet dimensions (including those commonly referred to as "microfluidic") the surface forces predominate. Similarly, due to the predominance of surface forces, modest volumes of fluids have difficulty passing through very small holes because the pressure from the weight of the fluid is insufficient to overcome the surface tension to pass through the hole.

In some embodiments of the invention, it is preferred that the closure reservoirs be of sufficiently small dimensions that the surface forces are able to hold fluids in place in them even when the earth's gravitational force tends to detach the fluids. For example, the closure of this embodiment of the invention may be a substantially flat lid for a well plate, and the reservoirs may be small hemispherical indentations in the lower surface of the lid. If these indentations are sufficiently small, even the maximum amount of fluid that they hold will be able to remain in place simply through surface forces in any orientation with respect to the earth's gravitational field.

In the invention it is preferred to be able to replenish the fluid in the closure reservoirs periodically. In this way, these reservoirs will always have an adequate supply of fluid, for example of solvent. This periodic replenishment could take place by removing the closure from the container, potentially inverting the closure or otherwise altering its orientation, and using some sort of fluid transport system to dispense fluid into the reservoirs through the openings that open into the interior of the container. The fluid transport system could be, for example, an automatic pipetting system, or a tip-based transport system, or an acoustic ejection system.

Alternatively, the closure could be designed in such a way that the replenishment can take place without removing the closure from the primary member of the container. Thus, for example, the closure could be designed to have a removable cover or plug, or alternatively a septum plug of a type which allows replenishment without removal, for example from a manufacturer such as ABgene (Epsom, United Kingdom). The reservoirs would have one or more openings which open into the interior of the container and another opening which is exposed when the removable cover or plug is removed. The replenishment of the fluid in the reservoirs of the closure could be performed by removing the cover or plug, dispensing fluid, and then replacing the cover or plug. With suitable control of the dispensing process so as to cause a low impact of the added fluid on the mass of fluid already present in the closure reservoirs, and if the openings that open into the interior of the container are sufficiently small, the addition of fluid would not cause any fluid to travel from the reservoirs into the interior of the container. It would be possible, for example, to dispense into reservoirs which do not have openings to the inside of the closure and then to allow the dispensed fluid to travel slowly through suitably sized channels from these reservoirs to other reservoirs which have such openings. The fluid transport system used could again be, for example, an automatic pipetting system, or a tip-based transport system, or an acoustic ejection system.

Figure 2A:
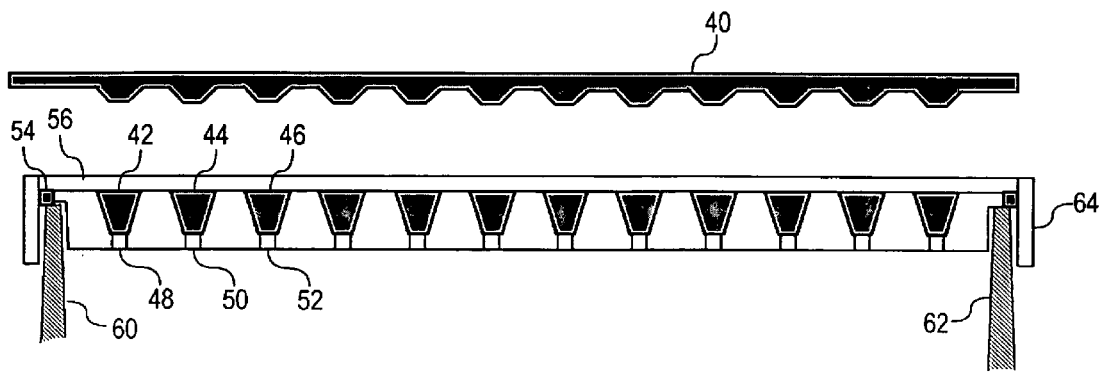
FIG. 2A-2B depict a schematic cross section and top view of a closure for a well plate which has a facility to allow replenishment of the supply of solvent in the closure reservoirs without removing the closure.
Figure 2B:
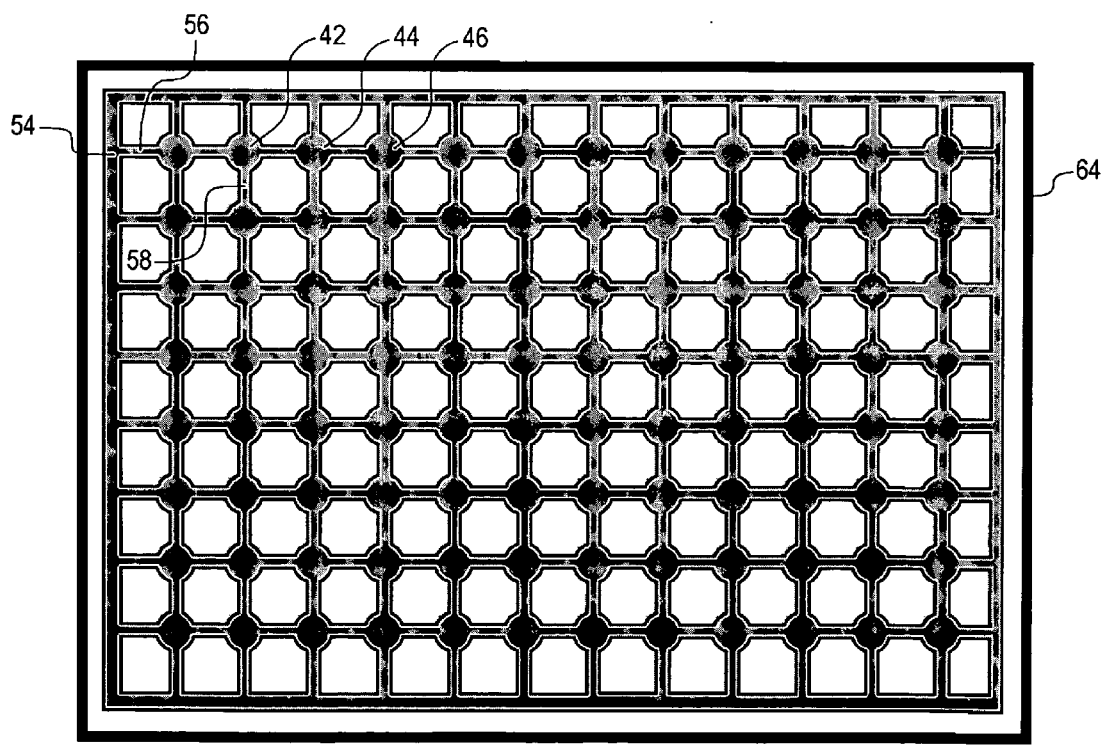

FIG. 2A-2B depict a schematic cross section and top view of a closure for a well plate which has a facility to allow replenishment of the supply of solvent in the closure reservoirs without removing the closure. FIG. 2A also depicts a cover 40 for the closure and projections 60, 62 from the primary member of the container which contact the closure. The closure 64 has a number of reservoirs 42, 44, 46 which can hold fluid. Between these reservoirs there run channels such as 56 and 58. Each reservoir has an opening such as 48, 50, 52 which allows evaporation of fluid to proceed downwards but is sufficiently small that gross movement of fluid downwards will not occur under conditions of use. The closure 64 also has a reservoir 54 which, as may be seen in the top view in FIG. 2B, runs all around the edge of the closure 64.

Figure 3:
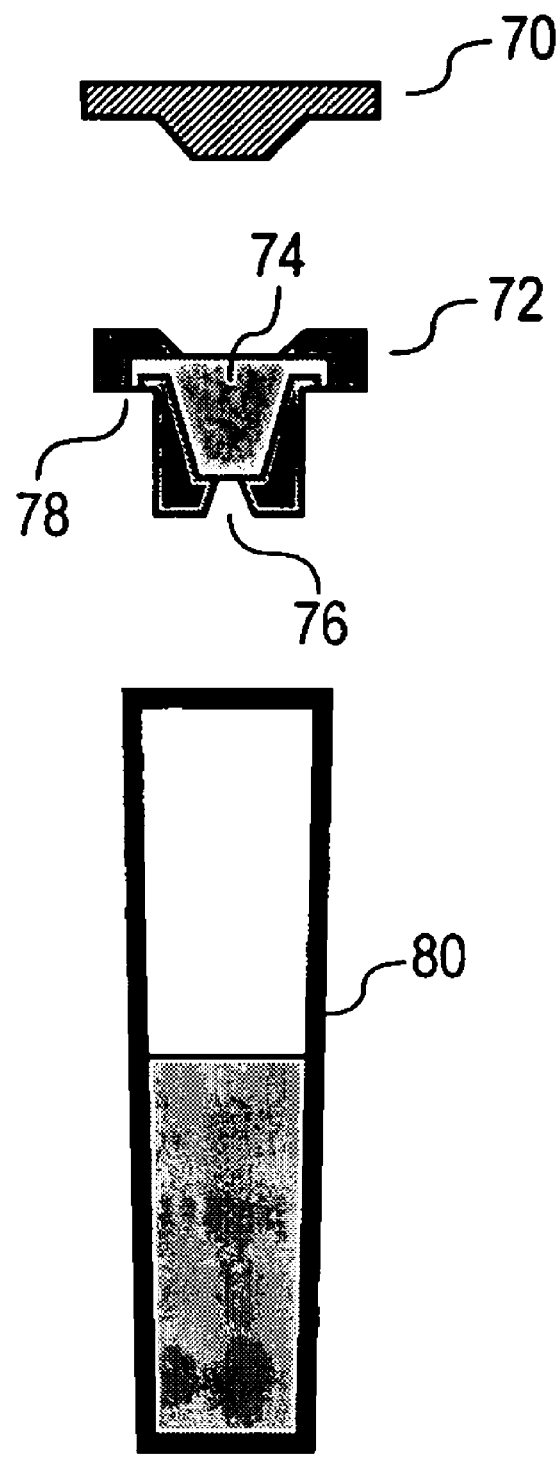
FIG. 3 depicts in schematic cross section a closure for a test tube which also has a facility to replenish the supply of solvent.

FIG. 3 depicts in schematic cross section a closure for a test tube 80 which also has a facility to replenish the supply of solvent. The closure 72 has a plug 70. It provides a reservoir 74 for fluids. The reservoir 74 has an opening 76 which allows evaporation of fluid to proceed downwards but is sufficiently small that gross movement of fluid downwards will not occur under conditions of use. There is also an opening 78 around the closure in the vicinity of the contact zone where the closure 72 contacts test tube 80.

As noted earlier, it is preferable that closures be capable of easy opening and closing. In many cases, the closures of the invention will be adapted to being opened and closed by means of robot arms of the type which are commonly used for the manipulation of containers in chemical and biomedical research. Thus, for example, it is preferable if the closure can be put in place by lowering it into position, and then opened simply by lifting it out of position. It is also preferred that the force of the earth's gravity suffice to hold the close in place. It is preferred that the force of the earth's gravity suffice to form the seal between closure and primary member.

Among the considerations which are relevant to the design of the closure the following may be noted. First, it preferred that the total volume of the container be reduced to something close to the minimum volume which is necessary to contain the fluids of interest. The greater the head space inside the container, the greater the amount of fluid that must evaporate to establish a partial pressure approaching the vapor pressure. Second, to the extent fluid is held in the closure reservoirs through surface forces, it is preferred that these surface forces be sufficient to retain the fluid in its position when the closure is subject to the inevitable forces which accompany the process of closure insertion and removal. Preferably, the process of insertion and removal does not subject the closure to significant forces, but in practice, to the extent this process is carried out by a human or by a general purpose robot arm, there will be some degree of impact of the closure on the primary member, resulting in a more or less sharp deceleration of the closure. It is preferred in particular that certain free surfaces of the fluid retained in the closure reservoirs lie approximately parallel to the direction of the impact force. Furthermore, it is possible to use mechanical design elements or foams in the closure reservoirs in order to improve the ability of the closure reservoir to retain fluid. Foams may include, for example, open-cell foams which have connected voids so they have the ability to hold substantial quantities of liquid and to allow the liquid to move throughout the extent of the foam. Where the solvent is DMSO, a foam that could withstand long-term exposure to DMSO like a polyethylene foams would be preferred. An open-cell polyethylene is OPCELL (described at http://www.chimeng.com.tw/e-opcell.htm) from Chi Meng Industry (Tainan, Taiwan). Third, while plugs and/or covers for the closure reservoirs are indicated as being desirable, it is also desirable to allow some ability for gases to enter and leave the closure reservoir as for example with a small vent. This ability prevents for example the formation of vacuums in any air space within the closure reservoir. The use of a commercially available septum plug may provide an adequate degree of venting for this purpose.

In order to facilitate the formation of a good seal, it is often desired that the portion of the closure which contacts the primary member be made of a compliant material. Compliance allows the closure to deform elastically to match the contour of the primary member when the closure is put into place, giving a tighter seal.

The choice of material for the formation of the closures and containers of the invention is constrained also by the need to be compatible with the fluids of interest. Among these, fluids where DMSO by itself or DMSO and water are solvents are of particular interest in chemical and biomedical research. Materials which are compatible with DMSO include cyclic olefin co-polymers (COC), polyethylene (PE), polypropylene (PP), ethylene-propylene rubber (EPR) and polytetrafluoroethylene (PTFE). COC is made by Ticona Engineering Polymers (Summit, N.J.), which is part of Celanese Corporation, and goes by the trade name Topas. One preferred Topas resin is 8007. These materials may advantageously be used to form the closures and primary members used in the invention. In general, the primary member and closure are preferably readily manufacturable, most preferably by injection molding of a single component or of two or three components subsequently brought together.

Under some circumstances the openings from closure reservoirs to the interior of the container may need to have a relatively large surface area for the exchange of vapor. This may occur, for example, if the volume of the fluids of interest is very small. In that case, even with a very good seal to the outside, an undesirable amount of evaporation may occur simply in order to fill the interior of the container with vapor. In order to prevent this, the closure reservoirs would need to be able to raise the partial pressure in the interior of the container fairly rapidly, which can be accomplished through a large surface area. Among the possibilities where a large surface area is required are openings with foams, gels, and similar materials which will allow gas diffusion but will not allow bulk movement of fluid, as well as a large number of small openings. It may be desirable, for example, for the surface area of the openings from the closure reservoirs to the interior to be 10%, 20%, or 100% of the surface area of the fluids of interest which are being held in the reservoirs of the primary member.

When designing a closure or container, the surface area of the fluids of interest when the container is in use may not be known, but it will often be possible to put an approximate or exact upper bound on that surface area based on the geometry of the container. The surface area of the openings from the closure reservoirs to the interior may then conveniently be chosen to be 10%, 20%, 100%, or some other suitable percentage of that upper bound. For many container forms, especially where the contact zone is approximately or exactly planar, a convenient rough upper bound is simply the area of the projection onto the plane of the contact zone of the surface of the closure or primary member which opens to the interior. For well plates, a convenient rough upper bound is the total cross sectional area of all wells. As will be perceived by those of skill in the art, this upper bound may be corrected for meniscus effects.

A further figure of merit which may be useful in the design of closure reservoirs is the percentage of the partial pressure of a solvent or other fluid inside the container which comes from the closure reservoirs when the closure is in place. Thus, for example, it could be specified that at least 10%, 20%, or 100% of the partial pressure should come from the closure reservoirs under particular conditions of fluid loading in the primary member.

Another figure of merit for closure reservoirs is the volume ratio of the closure reservoirs to the fluid of interest in the primary member. If this ratio were low, then as evaporation occurs the closure reservoirs would need fairly frequent replenishment. For this reason, it is preferable that the volume of the closure reservoirs be greater than 10% of the volume of the fluid of interest, preferably greater than 20%, or greater than 50% of the volume of the fluid of interest. When designing a closure or container, the volume of the fluids of interest that will be placed in the container when it is in use may not be known. For this reason, it may be convenient to design the volume of the closure reservoirs relative to the maximum volume which the primary member can hold or which fluids of interest can have, so that one has for example a closure reservoir volume greater than 1%, or greater than 5%, or greater than 10%, or greater than 20%, or greater than 50% of the maximum volume which the primary member reservoirs can hold.

Solvents used commonly in chemical and biomedical research may be hygroscopic. In particular, it is well known that DMSO is quite hygroscopic and that DMSO solutions will commonly draw humidity from the ambient air. In many circumstances this phenomenon whereby a fluid of interest comprising a hygroscopic solvent draws humidity from the ambient air is undesirable. A tight seal can thus help not only to keep evaporation from occurring but also to keep the fluids of interest from drawing undesirable humidity from the ambient air.

In connection with hygroscopic solvents, a further aspect of the invention is the use of humectants to draw moisture from the air. In particular, one or more reservoirs on the closure of the invention may be designed to contain a humectant. Such reservoirs are preferably arranged with openings on the outside of the container in the vicinity of the contact zone between closure and primary member.

Even if humectants are not employed, a closure reservoir which has been replenished with fresh hygroscopic solvent may have the advantage that it acts in effect as a humectant by attracting moisture preferentially in comparison to the fluids of interest.

In an alternative preferred embodiment of the invention, a container has a closure. The container has a primary member which contains one or more reservoirs for fluids of interest. The primary member could be, for example, a well plate or a test tube. The closure also contains one or more fluid reservoirs. At least some of these reservoirs have openings which open into the exterior of the container when it is closed using the closure, in the vicinity of the contact zone where the closure meets the primary member.

In a use of the container of the preceding embodiment, the fluids of interest are held within the reservoirs of the container. A solvent which the fluids of interest comprise is held in one or more closure reservoirs. The solvent evaporates from both the fluids of interest and from the closure reservoirs. The evaporation from the closure reservoirs causes the partial pressure of the solvent on the exterior of the container in the vicinity of the contact zone to rise. Since the rate at which the solvent diffuses from the interior of the container to the exterior is related to the difference of partial pressures of solvent immediately inside and outside the contact zone, it may be expected that evaporation from the closure reservoirs will tend to reduce the loss of solvent from the interior of the container.

A way of evaluating the effectiveness of the use of closure reservoirs with openings to the exterior of the container is to determine the partial pressure of the solvent of interest in the vicinity of the closure zone which is due to evaporation from the closure rather than from escape of the solvent through the seal. In that respect, it would be desirable if that pressure were 10%, preferably 20%, more preferably 50%, and more preferably 80% of the vapor pressure of the solvent of interest, so that diffusion of the solvent of interest through the seal is inhibited. An alternative figure of merit which may be considered in relation to this is what percentage of the partial pressure immediately outside the contact zone comes from the closure reservoirs rather than from the reservoirs containing the fluids of interest. A percentage of at least 10% or 20% of partial pressure from the closure reservoirs is preferred. Another figure of merit which may be considered in this regard is the ratio of fluid surface exposed by the closure reservoirs to the fluid surface exposed by the fluids of interest inside the container. If these surfaces are comparable, as for example where the ratio is close to 1, then because the vapors from the fluids of interest inside the container must pass through a seal and those from the closure reservoir do not, it may be expected that the bulk of the partial pressure of the solvent of interest in the vicinity of the contact zone will derive from the closure reservoirs.

A further advantage of having a closure reservoir exposed to the exterior of the container in the vicinity of the closure zone is the ability for a hygroscopic solvent in the closure reservoir, particularly fresh hygroscopic solvent resulting from replenishment, to act in effect as a humectant, attracting water vapor and reducing the concentration of water vapor in the vicinity of the closure zone and thus preventing the water vapor from entering the container.

It is generally, and in particular in the preceding embodiment, preferable if the container comprises some sort of structures which serve to slow the diffusion of gas outward from the contact zone. These structures in general will be structures which lengthen and narrow the diffusion path which gas takes when moving from the immediate exterior of the contact zone into the general atmosphere. A wide variety of such structures, sometimes referred to as "labyrinth seals," will occur to the person of skill in the art.

In general, a labyrinth seal seeks to increase the length of the path that a molecule in gas must travel from any of the fluids of interest to the outside of the container, or to open unobstructed ambient if the labyrinth is in whole or in part on the outside of the container. We may refer to this length as the "gas exchange path length." Projections in the closure or in the primary member may serve to increase this path if they serve as obstacles to gas diffusion. A measure of the effectiveness of a labyrinth seal is the increase in path length which it provides. Such increase for containers of the invention is preferably at least 1 mm, and more preferably at least 2 mm, and more preferably 1 cm. Compared to the gas exchange path length in the absence of the labyrinth seal, the gas exchange path length with the seal in place is preferably 25% more, and more preferably 100% more, than the length without the labyrinth seal. An alternative measure of labyrinth seal effectiveness looks at the number of changes of direction a molecule must undergo in order to trace a path from the surface of the fluid of interest closest to the outside in order to reach the outside.

As with the earlier embodiment of the invention where the closure reservoirs opened into the interior of the container, so with the preceding embodiment it may be desirable to replenish the fluid in the closure reservoirs. Such replenishment may take place as described earlier, either by removing the closure, or by providing openings by which the fluid may be replenished without removing the closure from the container, which openings may make use of a plug or cover.

As will be understood, there can be embodiments of this invention in which some closure reservoirs open into the interior of the container, and others open into the exterior of the container.

In particular, in a further embodiment of the invention, a closure reservoir may be designed so that the portion of the primary member which contacts the closure is partially surrounded by fluid when the closure and the primary members are in contact. Thus, this reservoir opens both into the interior and the exterior of the container when the latter is closed. This design creates a type of seal which bears some similarity to the water trap in household plumbing. Vapor from the interior of the container must pass through the fluid surrounding the contact zone in order to escape to the exterior of the container. As long as an adequate level of fluid is maintained surrounding the contact zone, such a seal can be quite effective in preventing evaporation as well as in limiting the inflow of water vapor. With this embodiment, it may be of particular interest to be able readily to replenish the level of fluid in the closure reservoir in which the contact between closure and primary member takes place. This reservoir, as will readily be understood, must conform to the shape of the primary member, so that for example if the primary member is a test tube the closure reservoir must be able to receive the annular open end of the test tube.

Alternatively, instead of a closure reservoir providing the fluid to immerse the portion of the primary member which contacts the closure, a reservoir on the primary member could be designed to provide fluid to immerse a portion of the closure which contacts the primary member. With this design, the fluid might desirably be replenished periodically. In that case, the closure could be provided with gaps or channels guiding replenishing fluid towards the contact zone to maintain fluid levels in a reservoir of the primary member encompassing or located near that zone.

FIG. 2A depicts an opening 54 which is in the vicinity of the contact zone and can serve to immerse in fluid the portion of the primary member, part of projection 60, which contacts the closure 64. FIG. 3 also depicts an opening 78 which is in the vicinity of the contact zone and can serve to immerse in fluid the portion of the primary member 80 which contacts the closure 72.

With the preceding embodiment, there may also be particular interest in having the portion of the closure which contacts the primary member be compliant. There may also be interest in having that portion of the closure have a compliance which increases when fluid is present, and in having that portion of the closure able to absorb fluid. In this regard, a class of polymers referred to as "sliding gels" has been studied, as shown for example by U.S. Pat. No. 6,828,378 and by the Ph.D. Thesis of M. van den Boogaard of the University of Groningen in The Netherlands, January, 2003 titled "Cyclodextrin-containing Supra-molecular Structures: From pseudo-polyrotaxanes towards molecular tubes, insulated molecular wires and topological networks." In the latter, at chapter 7, it is stated that a sliding gel as discussed there can absorb 35 and 25 times its dry weight in water or DMSO respectively.

Figure 4:
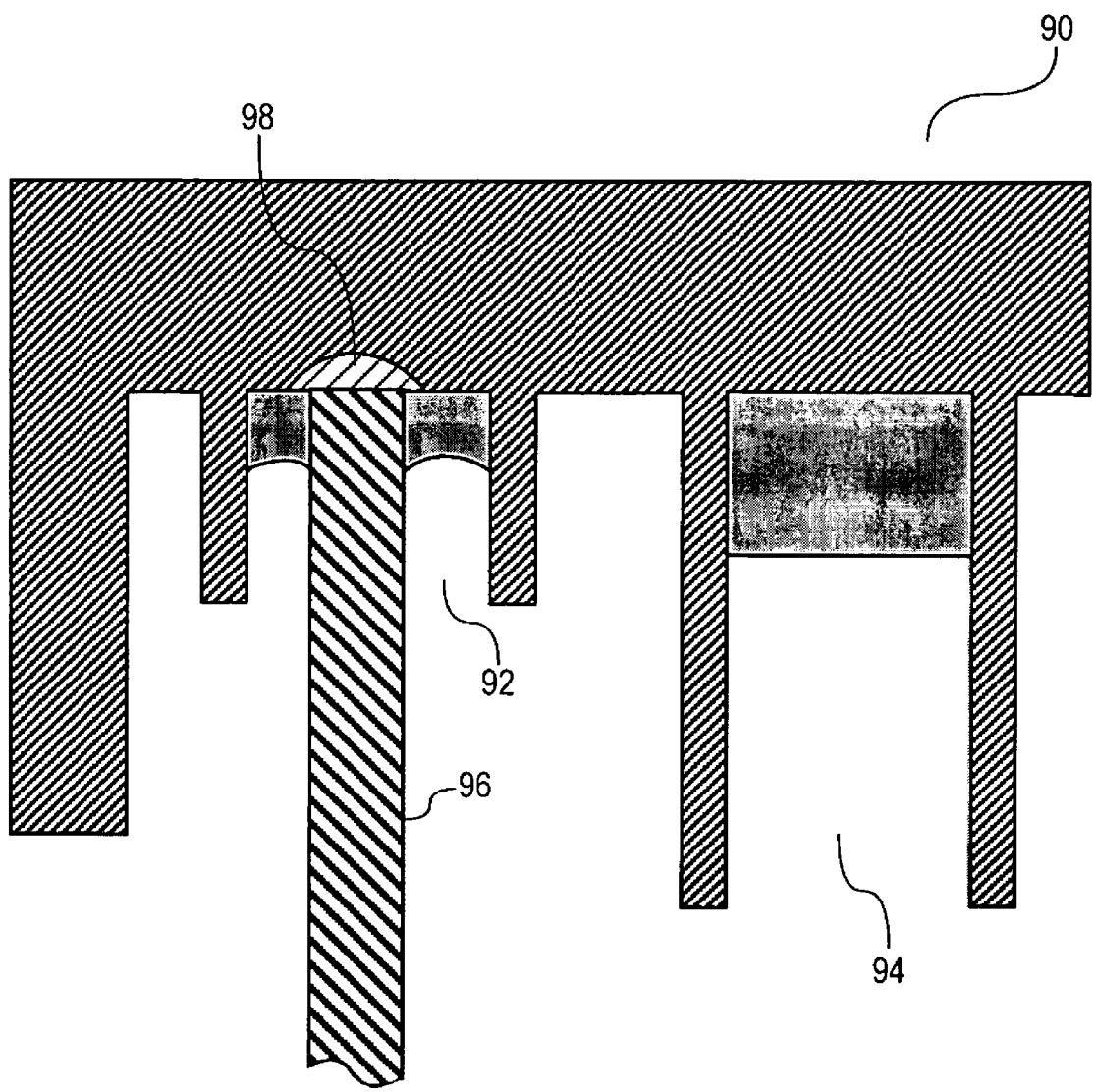
FIG. 4 depicts in schematic partial cross section a closure with a reservoir for fluid which surrounds a portion of the primary member which contacts the closure.

FIG. 4 depicts in schematic partial cross section a closure 90 with a reservoir for fluid 92 which surrounds a portion of the primary member, part of projection 96, which contacts the closure. The closure is also depicted as having an additional reservoir 94. At the top of reservoir 92 there is a volume 98 which is composed of a compliant material which absorbs fluid, for example a suitable sliding gel. The volume 98 can serve as a further reservoir of fluid to lessen the frequency with which the fluid in reservoir 92 is replenished.

Figure 5:
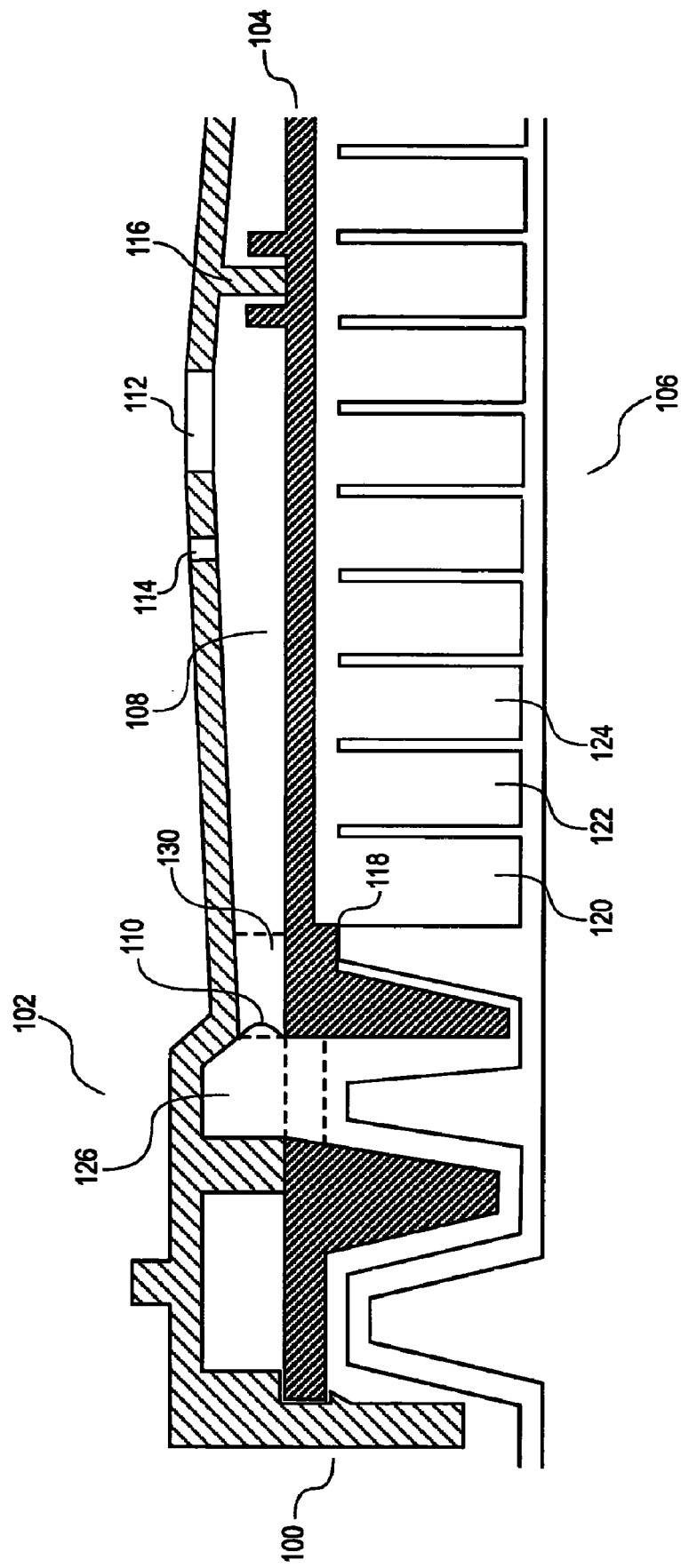
FIG. 5 depicts in schematic partial cross section an alternative preferred embodiment of the invention with a labyrinth seal and a single closure reservoir opening to the outside of the container close to the contact zone.

FIG. 5 depicts in schematic partial cross section an alternative preferred embodiment of the invention with a labyrinth seal and a single closure reservoir 108 with an opening 110 to the outside of the container, close to the contact zone 118. The closure 100 consists of an upper part 102 and a lower part 104, the lower part contacting the primary member 106 at the contact zone 118. The primary member 106 has a number of reservoirs 120, 122, 124 for fluids of interest. The lower part 104 of the closure approaches the tops of these reservoirs closely in order to lessen the container headspace. The upper part 102 of the closure is provided with a pluggable hole 112 for replenishing the fluid reservoir 108 without detaching the closure from the primary member 106. It is also provided with an optional vent hole 114 to facilitate the refilling process, and with structural support 116 to facilitate the process of plugging the hole 112. It may be seen that the reservoir 108 tapers towards the opening 110, becoming narrower as the opening is approached. The tapering draws the fluid towards the opening by capillary action. There are baffles 130 which provide further surface to hold fluid in reservoir 108. Additional features could be included in reservoir 108 to hold the fluid in place, for example additional baffles positioned elsewhere, spiral walls, or foam. The opening 110 allows fluid to evaporate into the volume 126 creating there a high partial pressure of the fluid, which as indicated above helps to reduce the rate at which the fluid exits through the imperfect seal at the contact zone 118. There is no opening from the reservoir 108 into the interior of the container, although such openings could be added if desired. As is seen in FIG. 5, the path that molecules in gas must followed to completely exit the container once it has passed through the seal at contact zone 118 has a number of bends, providing a labyrinth seal on the outside of the container. Despite the labyrinth seal, as may be seen the closure 100 comprising parts 102 and 104 may be lifted directly upwards when it is desired to open the container. When the closure is replaced atop the primary member 106, there will be an inevitable impact force. In this embodiment it is advantageous as noted earlier that this impact force is along the same direction as the fluid meniscus in opening 110.

In a further preferred embodiment of the invention, there are provided methods of storing fluids in containers. In certain methods of the invention, a fluid sample comprising a solvent is stored in a reservoir. The reservoir is covered using a closure which has one or more closure reservoirs. The closure reservoirs contain quantities of the solvent. The solvent in the closure reservoir is replenished.

The step of replenishment of the solvent, as noted above, preferably takes place in the methods of the invention without removing the closure from the container. For this purpose covers and plugs may be provided as already described.

In the methods of the invention, in particular, the fluids may be stored in well plates. When a well plate or other primary member is used which has multiple separated reservoirs for fluid, the methods apply to storing a number of fluids of interest, preferably having a common solvent. When the methods of the invention are practiced with well plates, it is common for the well plates to be stored by means of stacking. The closures of the invention are thus preferably designed in such a way that multiple containers of the invention stack comfortably and safely atop each other.

The methods of the invention are preferably carried out automatically. An overall laboratory automation system may include, for example, a carousel for holding well plates, a robot arm for moving well plates from one instrument to another, a variety of analytical instruments and reaction chambers, a pin based fluid transfer system, and/or an acoustic ejection system. The overall purposes of the system may include taking quantities of fluids and subjecting them to analyses (including for example the ascertainment of their composition and physical properties), reactions designed to produce particular moieties, and purification steps, all the while potentially keeping track, by computerized or other means, of the origin and destination of each fluid in the system and of the processes and results for each fluid. The system may also be employed to generate for further use objects which contain or are coated with fluids moved by the system.

The tracking of the origin, destination, processes, and results for each fluid may be performed, for example, by having controllers such as the fluid transport system controller communicate that information to a general purpose computer which stores the information as flat files or in a database. Fluids are conveniently identified by assigning an identifier to each well plate in the system and by tracking what is done to each well in each plate at particular times in a way that allows one to produce an overall history for the contents of each well of each plate. It must be kept in mind in this regard that not all changes in fluids in the system take place as a result of deliberate or planned action; some may be inevitable changes that occur as a result of the passage of time, as for example the absorption of water from the surrounding air or the evaporation of fluids in storage, which the containers and methods of the present invention are concerned with.

In a laboratory automation system it will generally be necessary to integrate equipment from different manufacturers. In this connection the adherence to particular standards may be a desirable feature of a fluid transport system. Certain fluid transport and storage systems which form part of a manufacturing environment may be required to meet further standards relating to manufacturing as well as being able to support overall system conformance with the norms of "Good Manufacturing Practice" (GMP) as understood by the pharmaceutical industry.

It is to be understood that while the invention has been described in conjunction with the preferred specific embodiments thereof, that the foregoing description and the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

We claim:

1. A method of storing a plurality of fluid samples all comprising a liquid solvent, the method comprising the steps of:
   (a) storing each of the plurality of fluid samples in a well of a well plate, each of the plurality of fluid samples including the liquid solvent;
   (b) covering the well plate with a closure which comprises a reservoir holding at least a first quantity of the liquid solvent and at least one opening which allows gas diffusion from the reservoir but does not allow liquid movement from the reservoir;
   (c) converting at least a part of the first quantity of the liquid solvent into a second quantity of a vapor solvent;
   (d) providing at least a part of the second quantity of the vapor solvent through the opening; and
   (e) replenishing the liquid solvent in the reservoir of the closure.

2. The method of claim 1, further comprising the step of:
   (f) covering the closure with a cover or plug which helps to prevent evaporation of the liquid solvent in the reservoir of the closure.

3. The method of claim 1, wherein the step (e) is carried out without removing the closure from the well plate.

4. The method of claim 1, wherein the step (e) is carried out by means of an automated pipetting system.

5. The method of claim 1, wherein the step (e) is carried out by means of an automated pin-based fluid transfer system.

6. The method of claim 1, further comprising the step of stacking the covered well plate atop other well plates.

7. The method of claim 1, wherein at least 10% of the vapor solvent escaping to the atmosphere through a seal between the closure and the well plate comes from the liquid solvent in the reservoir of the closure.

8. The method of claim 1, wherein the closure contacts the well plate at a contact zone, and wherein as a result of the presence of the liquid solvent in the reservoir of the closure, the partial pressure of the vapor solvent immediately outside the contact zone is at least 10% of the vapor pressure of the vapor solvent.

9. A method of storing a fluid sample comprising a liquid solvent, the method comprising the steps of:
  (a) placing the fluid sample in a first reservoir;
  (b) covering the first reservoir with a closure which includes a second reservoir holding at least a first quantity of the liquid solvent and at least one opening which allows gas diffusion to the first reservoir but does not allow liquid movement from the second reservoir to the first reservoir;
  (c) converting at least a part of the first quantity of the liquid solvent into a second quantity of a vapor solvent;
  (d) providing at least a part of the second quantity of the vapor solvent through the opening; and
  (e) replenishing the liquid solvent in the second reservoir.

10. The method of claim 9, further comprising the step of:
  (f) covering the closure with a cover or plug which helps to prevent evaporation of the liquid solvent in the second reservoir.

11. The method of claim 9, wherein the step (e) is carried out without removing the closure from the first reservoir.

12. The method of claim 9, wherein the step (e) is carried out by means of an automated pipetting system.

13. The method of claim 9, wherein the step (e) is carried out by means of an automated pin-based fluid transfer system.

14. The method of claim 9, wherein at least 10% of the vapor solvent escaping to the atmosphere through a seal between the closure and the first reservoir comes from the liquid solvent in the second reservoir.

15. The method of claim 9, wherein the closure contacts the first reservoir at a contact zone, and wherein as a result of the presence of the liquid solvent in the second reservoir, the partial pressure of the vapor solvent immediately outside the contact zone is at least 10% of the vapor pressure of the vapor solvent.

* * * * *